(12) United States Patent
Huang

(10) Patent No.: US 9,358,311 B2
(45) Date of Patent: Jun. 7, 2016

(54) GAS STERILIZATION APPARATUS

(75) Inventor: Ling-Huei Huang, Tainan (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 234 days.

(21) Appl. No.: 14/123,623

(22) PCT Filed: Jun. 10, 2011

(86) PCT No.: PCT/CN2011/000967
§ 371 (c)(1),
(2), (4) Date: Jan. 6, 2014

(87) PCT Pub. No.: WO2012/167401
PCT Pub. Date: Dec. 13, 2012

(65) Prior Publication Data
US 2014/0112837 A1    Apr. 24, 2014

(51) Int. Cl.
*A61L 2/00* (2006.01)
*A61L 2/20* (2006.01)

(52) U.S. Cl.
CPC .............. *A61L 2/0094* (2013.01); *A61L 2/202* (2013.01); *A61L 2202/11* (2013.01); *A61L 2202/123* (2013.01); *A61L 2202/24* (2013.01)

(58) Field of Classification Search
CPC .............................. A61L 2/0094; A61L 2/202
See application file for complete search history.

(56) References Cited

U.S. PATENT DOCUMENTS

| | | | | | |
|---|---|---|---|---|---|
| 5,207,993 | A | * | 5/1993 | Burris | A61L 2/202 210/138 |
| 5,520,893 | A | * | 5/1996 | Kasting, Jr. | C02F 1/78 422/117 |
| 5,811,014 | A | * | 9/1998 | Green | A61L 2/10 204/660 |
| 2007/0110824 | A1 | * | 5/2007 | Nageswaran | A01N 59/26 424/604 |
| 2008/0085211 | A1 | | 4/2008 | Huang | |

FOREIGN PATENT DOCUMENTS

| | | |
|---|---|---|
| CN | 1195298 A | 10/1998 |
| CN | 201399101 Y | 2/2010 |
| TW | M402738 | 5/2011 |
| WO | 00/10692 A1 | 3/2000 |

* cited by examiner

*Primary Examiner* — Jill Warden
*Assistant Examiner* — Matthew Krcha
(74) *Attorney, Agent, or Firm* — patenttm.us

(57) ABSTRACT

A gas sterilization apparatus comprises a housing with a sterilizing unit and a power device. An ozone generator and an air purifying device are provided in the housing. The power device is operated to allow air to pass through the ozone generator and flow into the sterilizing unit so as to perform sterilization. After being sterilized, the air in the sterilizing unit can be drained via the purification of the air purifying device. The gas sterilization apparatus can sterilize the air by use of ozone, thus it is applicable for articles and materials which can be sufficiently soaked by ozone to achieve the sterilization effect, and it can reduce the denaturation of biological materials, so it has wide application. The gas sterilization apparatus can sterilize the articles and materials in simple and convenient ways for user, so it is beneficial to use in the industry.

6 Claims, 5 Drawing Sheets

GAS STERILIZATION APPARATUS

FIELD OF THE INVENTION

The present invention relates to a gas sterilization apparatus, especially to an apparatus for sterilizing biological materials with ozone.

BACKGROUND OF THE INVENTION

Typically, biological materials refer to materials existing in or derived from living organisms. As the biological materials possess excellent biocompatibility, the biological materials are widely used in medical applications. To ensure safety of using the biological materials, the biological materials must be subjected to a strict sterilizing procedure in order to be suitable for use in living organisms.

Conventional methods for sterilizing the biological materials are as follows:

(1) Sterilization with 75% ethanol: immersing the biological materials in 75% ethanol. The disadvantage of this method is that the biological materials are easily denatured. Moreover, prior to use, the biological materials need to be rinsed. However, the rinsing may not completely remove the ethanol and ethanol residue may remain in the biological materials.

(2) Sterilization with radiation: irradiating the biological materials with rays or ultraviolet radiation to sterilize the biological materials. However, the energy of the rays is so high that some chemical structures of the biological materials are destroyed. Moreover, irradiating the biological materials with the rays has to be operated in a specific place with specific equipment. In addition, the ultraviolet radiation has a limited penetration distance, so is inefficient in sterilizing the biological materials that are mostly in three-dimensional shape.

(3) Sterilization with chemical bactericides: adding chemical bactericides into the biological materials to sterilize the biological materials. However, most of the chemical bactericides are toxic and are difficult to be removed. Therefore, sterilizing the biological materials with the chemical bactericides is only used in few fields and is impractical.

(4) Sterilization under high temperature and high pressure: this method results in denaturation of the biological material easily, even completely losing bioactivity of the biological material.

Each of the aforementioned sterilization methods has its drawbacks. People skilled in the art are anxious to design a sterilization apparatus that can be easily and widely used without causing damage to the biological materials.

SUMMARY OF THE INVENTION

The main objective of the present invention is to provide a gas sterilization apparatus to overcome the inconvenience and the shortcomings of destruction of structures of biological materials when sterilizing the biological materials with the conventional sterilizing methods.

The gas sterilization apparatus comprises a housing having an assembling chamber, a dust accumulating unit, and a sterilizing unit mounted in the housing, the dust accumulating unit disposed close to the sterilizing unit; a power device including a driving assembly and a control switch, the driving assembly including a first pump and a second pump, an inlet end of the second pump connected to and communicating with the sterilizing unit via pipes, and the control switch electrically connected to the driving assembly; an ozone generator mounted in the assembling chamber, and connected to and communicating with an outlet end of the first pump and the dust accumulating unit via pipes; and an air purifying device mounted in the assembling chamber and including an antibacterial ceramic and a filter assembly, the antibacterial ceramic having an inlet and an outlet, the outlet connected to and communicating with an inlet end of the first pump and the sterilizing unit, and the filter assembly connected to and communicating with an outlet end of the second pump via pipes to exhaust sterilized gas.

In the aforementioned gas sterilization apparatus, the dust accumulating unit has a first dust accumulating chamber and a second dust accumulating chamber. The first dust accumulating chamber is connected to and communicates with the ozone generator via pipes. The first dust accumulating chamber communicates with the second dust accumulating chamber with a filter mounted between the first dust accumulating chamber and the second dust accumulating chamber. The second dust accumulating chamber communicates with the sterilizing unit with another filter mounted between the second dust accumulating chamber and the sterilizing unit.

In the aforementioned gas sterilization apparatus, the first dust accumulating chamber is disposed below the second dust accumulating chamber, and the dust accumulating unit is disposed between the assembling chamber and the sterilizing unit.

In the aforementioned gas sterilization apparatus, the first dust accumulating chamber and the second dust accumulating chamber are disposed next to each other, the dust accumulating unit is disposed below the sterilizing unit, and the assembling chamber is disposed at the same side as the dust accumulating unit and the sterilizing unit.

In the aforementioned gas sterilization apparatus, the filter assembly includes a first activated carbon filtration core and a second activated carbon filtration core. The first activated carbon filtration core is connected to and communicates with the outlet end of the second pump and the second activated carbon filtration core via pipes. An exhaust pipe is connected to the second activated carbon filtration core to exhaust gas.

The present invention has the following advantages. A user may put articles and materials that are intended to be sterilized in the sterilizing unit in the housing, and turn on the control switch to allow the first pump to force exterior air to flow through the antibacterial ceramic and toward the ozone generator to become ozone-rich gas. Then the ozone-rich gas flows to the dust accumulating unit to be filtered, and flows to the sterilizing unit to be sterilized. The sterilized gas can be forced by the second pump to flow into the filter assembly to be purified, and then can be exhausted to the exterior. The gas sterilization apparatus in accordance with the present invention can sterilize the articles and the materials in simple and convenient ways, and use of the gas sterilization apparatus is not restricted by location. Moreover, sterilizing the biological materials with ozone can reduce denaturation of the biological materials and is suitable for the biological material in three-dimensional shape. Thus, the gas sterilization apparatus can sterilize the articles and materials in simple and convenient ways for the user, so it is beneficial for industrial use.

REFERENCE NUMBER LIST

10—housing; 11—assembling chamber; 12—dust accumulating unit; 13—sterilizing unit; 14—first dust accumulating chamber; 15—second dust accumulating chamber; 16—filter; 20—power device; 21—driving assembly; 22—first pump; 23—second pump; 24—control switch; 25—button; 30—ozone generator; 40—air purifying device; 41—antibacterial ceramic; 42—inlet; 43—outlet; 44—three-way pipe; 45—filter assembly; 46—first activated carbon filtration core; 47—second activated carbon filtration core; 48—exhaust pipe.

DETAILED DESCRIPTION OF THE EMBODIMENTS

The following descriptions of the preferred embodiments of the present invention are accompanied with the aforementioned attached drawings to explain the techniques for achieving the objective of the present invention.

FIGS. 1 to 6 show some embodiments of a gas sterilization apparatus in accordance with the present invention. The gas sterilization apparatus comprises a housing 10, a power device 20, an ozone generator 30, and an air purifying device 40.

Figure 1:
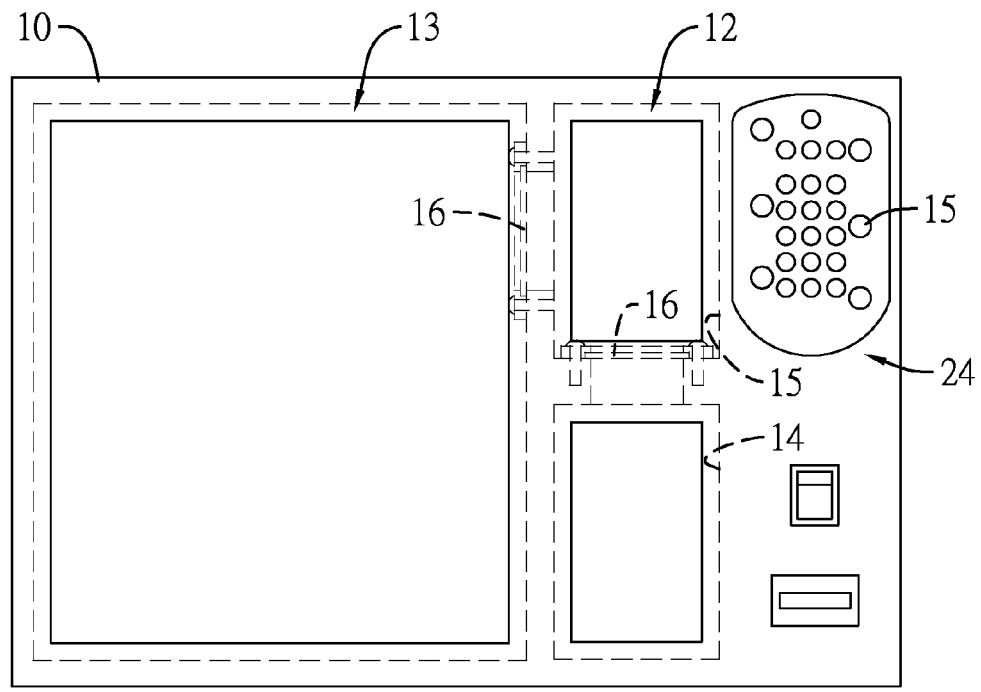
FIG. 1 is a schematic front view of a first embodiment of a gas sterilization apparatus in accordance with the present invention.
Figure 2:
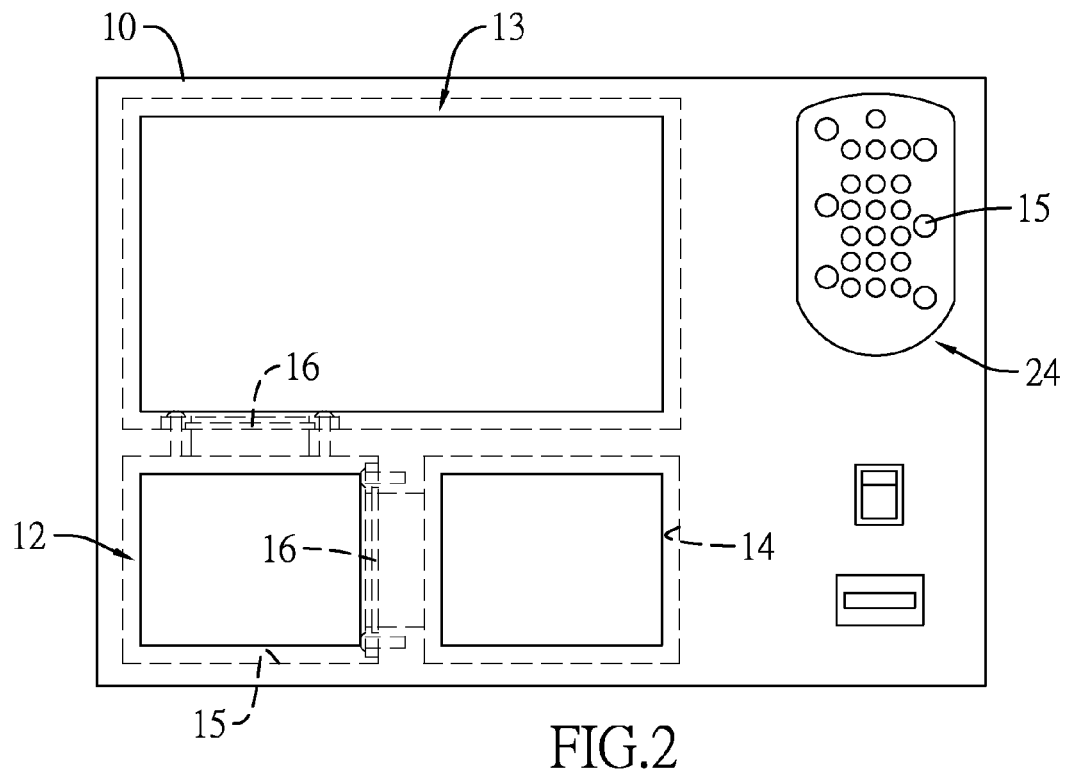
FIG. 2 is a schematic front view of a second embodiment of a gas sterilization apparatus in accordance with the present invention.

The housing 10 has an assembling chamber 11, a dust accumulating unit 12, and a sterilizing unit 13 mounted in the housing 10. The dust accumulating unit 12 has a first dust accumulating chamber 14 and a second dust accumulating chamber 15. The sterilizing unit 13 is for placing biological materials in order to sterilize the biological materials. The first dust accumulating chamber 14 communicates with the second dust accumulating chamber 15, and a filter 16 is mounted between the first dust accumulating chamber 14 and the second dust accumulating chamber 15. The second dust accumulating chamber 15 communicates with the sterilizing unit 13, and another filter 16 is mounted between the second dust accumulating chamber 15 and the sterilizing unit 13. As shown in FIG. 1, the first dust accumulating chamber 14 and the second dust accumulating chamber 15 are disposed next to each other. The dust accumulating unit 12 is disposed below the sterilizing unit 13, and the assembling chamber 11 is disposed at the same side as the dust accumulating unit 12 and the sterilizing unit 13. Alternatively, as shown in FIG. 2, the first dust accumulating chamber 14 is disposed below the second dust accumulating chamber 15, and the dust accumulating unit 12 is disposed between the assembling chamber 11 and the sterilizing unit 13. In the aforementioned description, a door is mounted on the housing 10 to selectively open or close the sterilizing unit 13, and a cover is mounted on the housing 10 to selectively close the first and the second dust accumulating chambers 14, 15.

Figure 3:
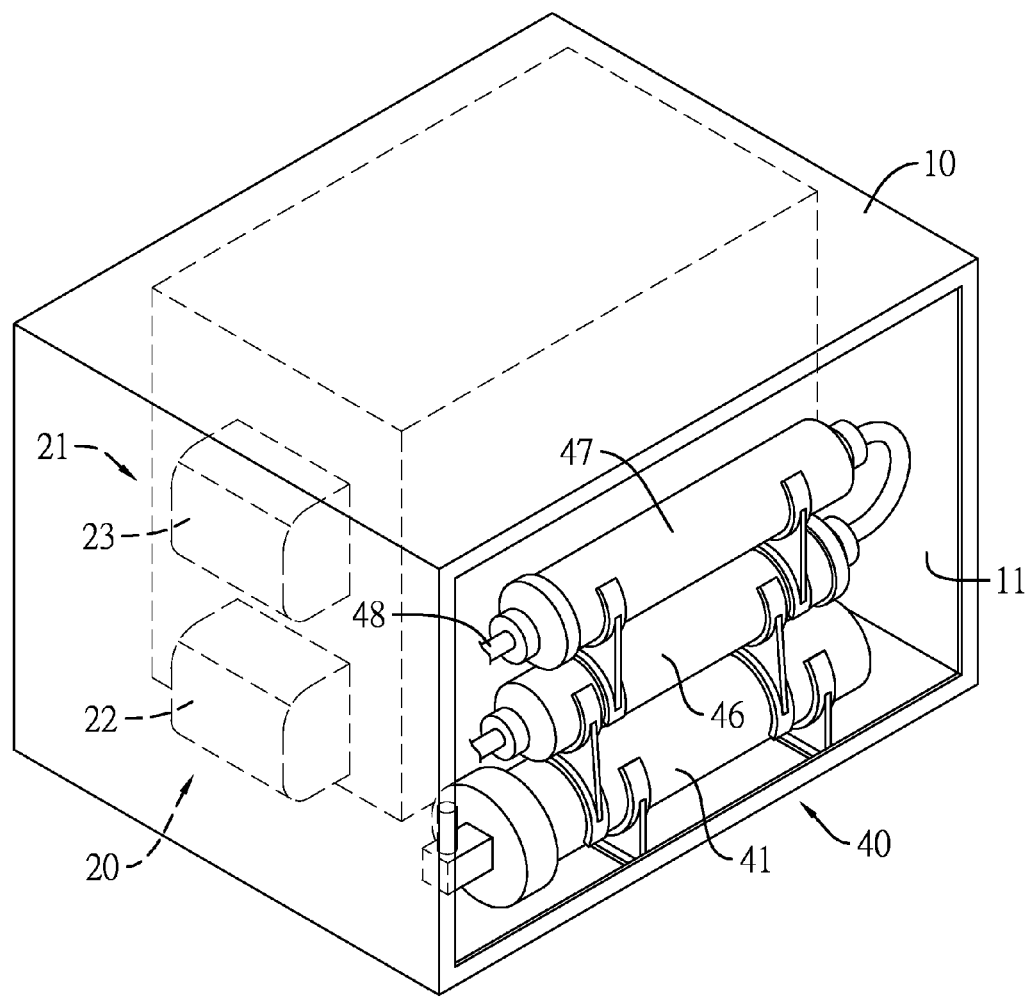
FIG. 3 is a perspective schematic rear view of the first embodiment of the gas sterilization apparatus in accordance with the present invention.

The power device 20 includes a driving assembly 21 and a control switch 24. The driving assembly 21 can be mounted outside the housing 10 or be mounted in the assembling chamber 11 of the housing 10 to drive fluid to flow (as shown in FIG. 3). The driving assembly 21 includes a first pump 22 and a second pump 23. An inlet end of the second pump 23 is connected to and communicates with the sterilizing unit 13 via pipes. The control switch 24 is electrically connected to an external power source, and is electrically connected to the first pump 22 and the second pump 23. The control switch 24 has multiple buttons 25 and is exposed to an exterior of the housing 10 for the convenience of operating.

The ozone generator 30 is also mounted in the assembling chamber 11, and is connected to and communicates with an outlet end of the first pump 22 and the first dust accumulating chamber 14 via pipes. Gas that is driven by the first pump 22 and flows into the ozone generator 30 becomes ozone-rich gas.

The air purifying device 40 is also mounted in the assembling chamber 11 (as shown in FIG. 3). The air purifying device 40 includes an antibacterial ceramic 41 and a filter assembly 45. The antibacterial ceramic 41 has an inlet 42 and an outlet 43. A three-way pipe 44 is connected to the outlet 43, and is connected to and communicates with an inlet end of the first pump 22 and the sterilizing unit 13 via pipes.

Exterior air flows into the antibacterial ceramic 41 through the inlet 42, and selectively flows into the first pump 22 or the sterilizing unit 13 via the three-way pipe 44. The filter assembly 45 includes a first activated carbon filtration core 46 and a second activated carbon filtration core 47. The first activated carbon filtration core 46 is connected to and communicates with an outlet end of the second pump 23 and the second activated carbon filtration core 47 via pipes. An exhaust pipe 48 for exhausting sterilized gas is connected to the second activated carbon filtration core 47.

Figure 4:
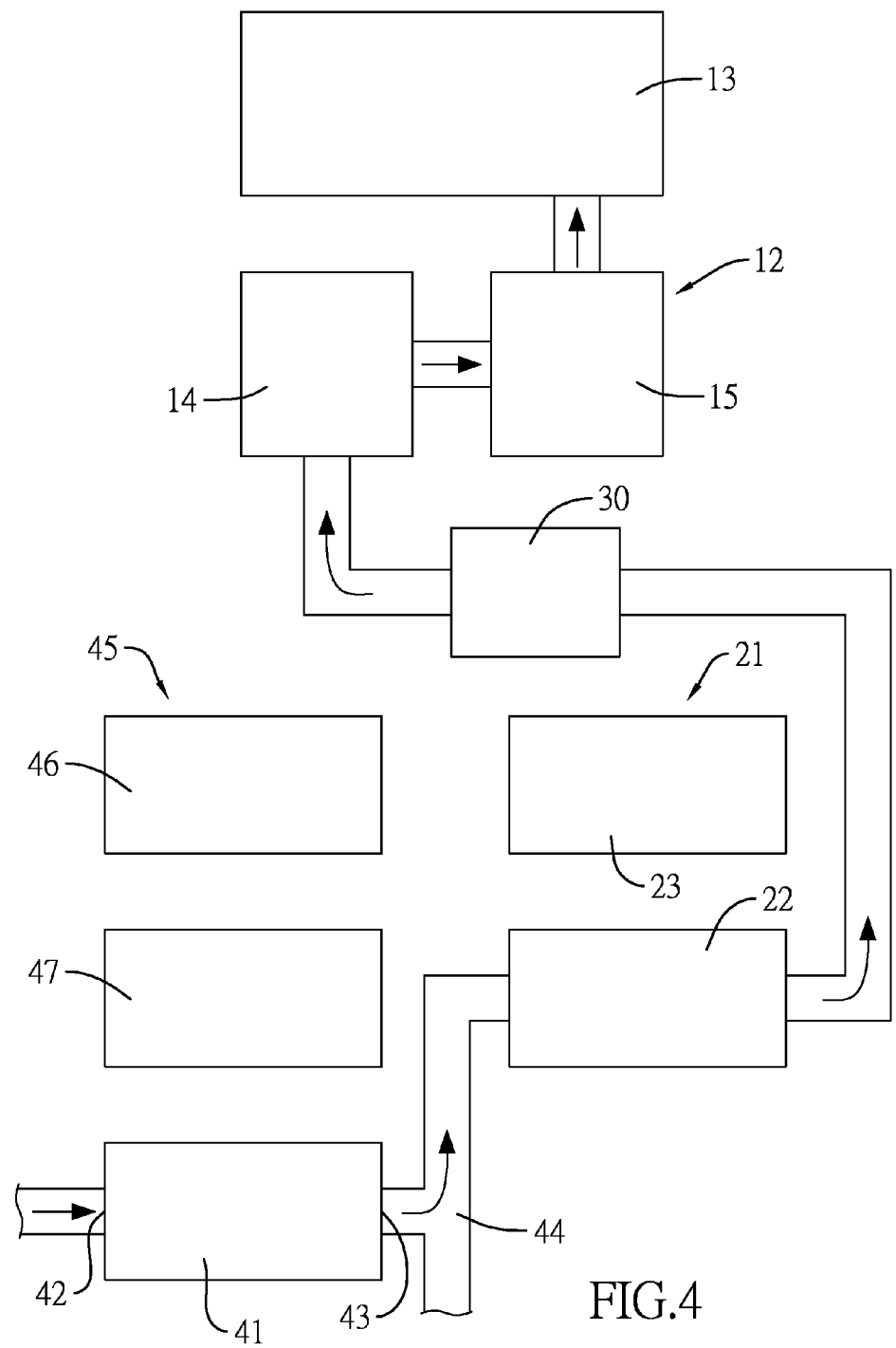
FIG. 4 is a schematic flow chart of the gas sterilization apparatus in accordance with the present invention, shown sterilizing.

As shown in FIG. 4, a user puts articles and materials that are intended to be sterilized in the sterilizing unit 13, and turns on the control switch 24 to drive the first pump 22. The exterior air flows through the inlet 42 of the antibacterial ceramic 41 first, flows into the first pump 22 via the three-way pipe 44, and then flows into the ozone generator 30 to become ozone-rich gas. The ozone-rich gas further flows into the first dust accumulating chamber 14, flows into the second dust accumulating chamber 15 through the filter 16, and then flows into the sterilizing unit 13 through the filter 16 to sterilize the articles and the materials placed in the sterilizing unit 13 with ozone. Some of the impurities in the gas are deposited in the first and the second dust accumulating chambers 14, 15.

Figure 5:
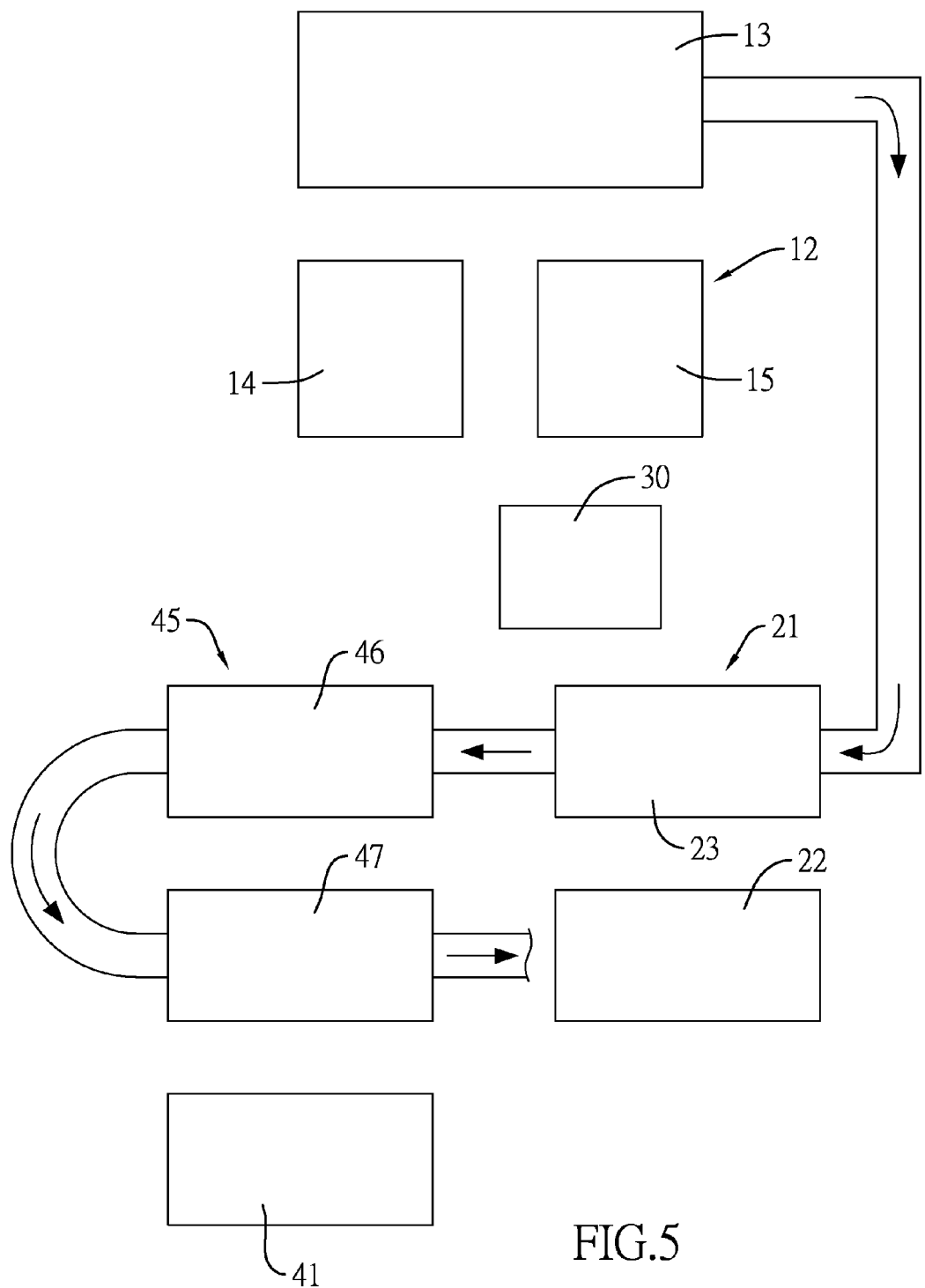
FIG. 5 is a schematic flow chart of the gas sterilization apparatus in accordance with the present invention, shown exhausting after sterilizing.

As shown in FIG. 5, after the ozone-rich gas sterilizes the articles and the materials in the sterilizing unit 13, the second pump 23 is driven to guide the ozone-rich gas to the first activated carbon filtration core 46 and then to the second activated carbon filtration core 47 to purify the ozone-rich gas with the filter assembly 45. Thus, the ozone-rich gas can be exhausted to an exterior safely.

Figure 6:
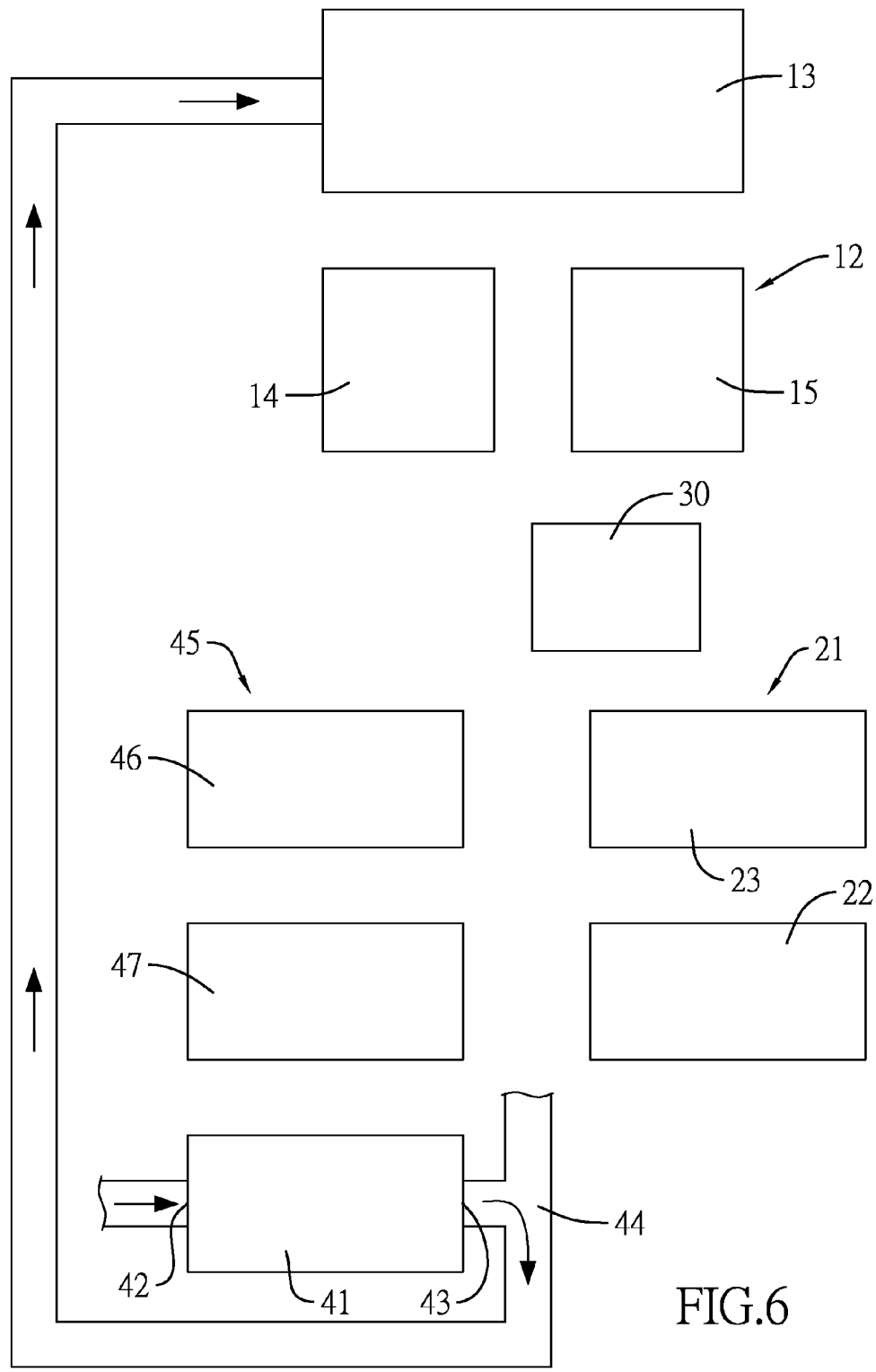
FIG. 6 is a schematic flow chart of the gas sterilization apparatus in accordance with the present invention, shown inflating after sterilizing.

As shown in FIG. 6, the fresh air that flows through the antibacterial ceramic 41 can selectively flow directly into the sterilizing unit 13 via the three-way pipe 44 to supplement air pressure in the sterilizing unit 13 in order to benefit the subsequent sterilization operation.

In sum, the gas sterilization apparatus sterilizes the articles and the materials with the ozone. With the gas that diffuses, sterilizing with ozone can be used on the biological material in three-dimensional shape. With sterilizing characteristic of the ozone, the gas sterilization apparatus can sterilize multiple kinds of articles and materials without causing denaturation of the articles and the materials. Furthermore, the gas sterilization apparatus does not emit radiation during operation, so use of the gas sterilization apparatus is safe and is not restricted by location. Therefore, the gas sterilization apparatus is simple, convenient, and practical for use, meets the user's need, and benefits the industry.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A gas sterilization apparatus comprising:
a housing having an assembling chamber, a dust accumulating unit, and a sterilizing unit mounted in the housing, the dust accumulating unit disposed close to the sterilizing unit, the dust accumulating unit having a first dust accumulating chamber and a second dust accumulating chamber, the first dust accumulating chamber communicating with the second dust accumulating chamber with a filter mounted between the first dust accumulating chamber and the second dust accumulating chamber, and the second dust accumulating chamber communicating with the sterilizing unit with another filter mounted between the second dust accumulating chamber and the sterilizing unit;
a power device including a driving assembly and a control switch, the driving assembly including a first pump and a second pump, an inlet end of the second pump connected to and communicating with the sterilizing unit via pipes, and the control switch electrically connected to the driving assembly;
an ozone generator mounted in the assembling chamber, and connected to and communicating with an outlet end of the first pump and the first dust accumulating chamber of the dust accumulating unit via pipes; and
an air purifying device mounted in the assembling chamber and including an antibacterial ceramic and a filter assembly, the antibacterial ceramic having an inlet and an outlet, the outlet connected to and communicating with an inlet end of the first pump and the sterilizing unit, and the filter assembly connected to and communicating with an outlet end of the second pump via pipes to exhaust sterilized gas.

2. The gas sterilization apparatus as claimed in claim 1, wherein the first dust accumulating chamber is disposed below the second dust accumulating chamber, and the dust accumulating unit is disposed between the assembling chamber and the sterilizing unit.

3. The gas sterilization apparatus as claimed in claim 1, wherein the first dust accumulating chamber and the second dust accumulating chamber are disposed next to each other, the dust accumulating unit is disposed below the sterilizing unit, and the assembling chamber is disposed at the same side as the dust accumulating unit and the sterilizing unit.

4. The gas sterilization apparatus as claimed in claim 1, wherein the filter assembly includes a first activated carbon filtration core and a second activated carbon filtration core, the first activated carbon filtration core is connected to and communicates with the outlet end of the second pump and the second activated carbon filtration core via pipes, and an exhaust pipe is connected to the second activated carbon filtration core to exhaust gas.

5. The gas sterilization apparatus as claimed in claim 2, wherein the filter assembly includes a first activated carbon filtration core and a second activated carbon filtration core, the first activated carbon filtration core is connected to and communicates with the outlet end of the second pump and the second activated carbon filtration core via pipes, and an exhaust pipe is connected to the second activated carbon filtration core to exhaust gas.

6. The gas sterilization apparatus as claimed in claim 3, wherein the filter assembly includes a first activated carbon filtration core and a second activated carbon filtration core, the first activated carbon filtration core is connected to and communicates with the outlet end of the second pump and the second activated carbon filtration core via pipes, and an exhaust pipe is connected to the second activated carbon filtration core to exhaust gas.

* * * * *